United States Patent [19]

Takahashi et al.

[11] Patent Number: 4,981,799

[45] Date of Patent: Jan. 1, 1991

[54] ACYLAMINO ACID RACEMASE, PRODUCTION AND USE THEREOF

[75] Inventors: Takeshi Takahashi, Izumi; Kazunori Hatano, Kawanishi, both of Japan

[73] Assignee: Takeda Chemical Industries, Ltd., Osaka, Japan

[21] Appl. No.: 227,882

[22] Filed: Aug. 3, 1988

[30] Foreign Application Priority Data

Aug. 21, 1987 [JP] Japan ................................ 62-208484

[51] Int. Cl.$^5$ ............................................... C12N 9/90
[52] U.S. Cl. ...................................... 435/233; 435/280
[58] Field of Search ................................ 435/233, 280

[56] References Cited

U.S. PATENT DOCUMENTS 3,991,077  11/1976  Uzuki et al. ................ 260/326.14
4,602,096   7/1986  Karrenbauer et al. ............ 548/498

FOREIGN PATENT DOCUMENTS 2352579  5/1974  Fed. Rep. of Germany .
3712539  2/1988  Fed. Rep. of Germany .
2586702  3/1987  France .

OTHER PUBLICATIONS

Soda et al.—Chem. Abst., vol. 105, (1986), p. 96047f.

Soda et al., Biochemical and Biophysical Research Communications, vol. 35, No. 3, pp. 363–368, (1969).

Bergmann et al., Biochemische Zeitschrift, vol. 203, pp. 280–292, (1928).

Behr et al., Journal of the American Chemical Society, vol. 54, pp. 1630–1693, (1932).

Fukumura, Agricultural and Biological Chemistry, vol. 40, No. 9, pp. 1687–1693, (1976).

Chibata et al., Bulletin of the Agricultural Chemical Society of Japan, vol. 21, No. 5, pp. 300–303, (1957).

Kinoshita et al., Journal of General and Applied Microbiology, vol. 3, No. 3, pp. 193–204, (1957).

Yamada et al., Journal of Fermentation Technology, vol. 56, No. 5, pp. 484–491, (1978).

*Primary Examiner*—Sam Rosen
*Attorney, Agent, or Firm*—Wenderoth, Lind & Ponack

[57] ABSTRACT

The present invention relates to acylamino acid racemase, production and use thereof.

The acylamino acid racemase of the present invention racemizes optically active N-acyl-α-aminocarboxylic acid alone at pH values around the neutral level at a normal temperature under normal pressure in the presence of optical active amino acid; its use in combination with D- or L-aminoacylase enables the production of optically active D- or L-α-amino acid from DL-acyl-α-aminocarboxylic acid at a high level of efficiency.

6 Claims, 3 Drawing Sheets

ACYLAMINO ACID RACEMASE, PRODUCTION AND USE THEREOF

The present invention relates to an acylamino acid racemase, production and use therof.

The reaction by which optically active N-acyl-α-aminocarboxylic acid (hereinafter referred to as $N^\alpha$-acylamino acid) is racemized to optically inactive DL-N-acylamino acid is an important reaction used to produce optically active amino acids.

The known production methods for DL-$N^\alpha$-acylamino acid by racemization of optically active $N^\alpha$-acylamino acid are limited to physical or chemical methods under severe conditions, for example, the method in which the starting material, together with a less than equivalent amount of acetic anhydride, is heated in acetic acid [Biochem. Z., 203,280 (1929)], the method in which the starting material, together with a large amount of acetic anhydride, is treated at room temperature [J. Am. Chem. Soc., 54, 1630 (1932)], the method in which the starting material is heated in a solvent such as phosphoric acid triester or lower fatty acid [Japanese published examined patent application No. 18402/1976], the method in which optically active $N^\alpha$-acylamino acid is directly heated at about 160° C. in a nitrogen gas flow [Japanese published unexamined patent application No. 126058/1986] and the method in which the starting material, together with a catalytic amount of a dehydrating agent, is heated above 130° C. in the presence of an aromatic hydrocarbon [Japanese published unexamined patent application No. 165354/1986].

The racemization of D-$N^\alpha$-acylamino acid has been used in combination with aminoacylase to produce optically active L-α-amino acids. Thus, by means of catalytic action of aminoacylase, the inexpensive starting material DL-$N^\alpha$-acylamino acid is converted into L-α-amino acid and D-$N^\alpha$-acylamino acid, which are separated on the basis of physical property differences and are each isolated. Any one of the physical or chemical racemization methods is then applied to the D-$N^\alpha$-acylamino acid to convert it into the starting material DL-$N^\alpha$-acylamino acid, which is again treated with aminoacylase. By repeating this procedure, the starting material DL-$N^\alpha$-acylamino acid can be completely converted to the optically active L-α-amino acid. However, this method has a major drawback. A separation procedure is required for mutual separation of L-α-amino acid and N-acylamino acid following the reaction by aminoacylase. Also, the racemization procedure for the D-$N^\alpha$-acylamino acid must be performed under chemically or physically severe conditions after isolated in a solid form.

If this racemization can be achieved selectively for D-$N^\alpha$-acylamino acid alone in the presence of an optically active amino acid under such conditions that aminoacylase is not inactivated (in a nearly neutral aqueous solution at room temperature under normal pressure), such selective racemization, in cooperation with aminoacylase, will enable 100% conversion in one step of the starting material DL-$N^\alpha$-acylamino acid to the desired product L-α-amino acid without any separation procedure. It will be possible to dispense with the separation and racemization procedures which are mandatory for the prior art, and efficiency will be greatly increased in the production process for optically active amino acids.

However, it is not possible to achieve selective racemization under any conditions of the prior art. One possible way to accomplish this is to obtain an enzyme or racemizing agent which possesses the selectivity such that it acts on optically active $N^\alpha$-acylamino acid to racemize it but does not act on the corresponding optically active α-amino acid. However, an enzyme or racemizing agent exhibiting such a catalytic action has not been recognized thus far. It is well-known that there exist the enzymes which do not act on $N^\alpha$-acylamino acid but which act on optically active α-amino acid to racemize it, namely what are called amino acid racemases [Biochem. Biophys. Res. Comm., 35,363 (1969), for instance]. It is evident, however, these amino acid racemases cannot be used for this purpose.

The present inventors made investigations and for the first time demonstrated that there is a naturally-occurring enzyme which does not act on optically active amino acids but which acts on optically active $N^\alpha$-acylamino acids to convert it into the corresponding enantiomorphs and named this enzyme acylamino acid racemase. The present inventors made further studies and established a method of producing optically active α-amino acid from DL-$N^\alpha$-acylamino acid by means of acylamino acid racemase.

Accordingly, the present invention relates to an enzyme acylamino acid racemase which has the following properties;

(1) converting D-$N^\alpha$-acylamino acid to the corresponding L-$N^\alpha$-acylamino acid, (2) converting L-$N^\alpha$-acylamino acid to the corresponding D-$N^\alpha$-acylamino acid,

(3) not converting D-α-amino acid to the corresponding L-α-amino acid, and (4) not converting L-α-amino acid to the corresponding D-α-amino acid;

to a method for producing the acylamino acid racemase, which comprises cultivating a microorganism capable of producing said enzyme in a culture medium to accumulate said enzyme in the broth and harvesting said enzyme; and to a method for producing optically active D-or L-amino acid which comprises contacting DL-$N^\alpha$-acylamino acid with the acylamino acid racemase in the presence of D- or L- aminoacylase.

For the above $N^\alpha$-acylamino acid and α-amino acid, the α-amino acid may be of either the natural type or the non-natural type. Also, it does not matter whether the α-amino acid is neutral, basic or acidic.

For example, the $N^\alpha$-acylamino acid above may be shown by the formula:

$$X-NH-\underset{H}{\overset{R}{C}}-COOH \qquad (I)$$

wherein X is carboxylic acid derived acyl which may be substituted, and R is $C_{1-20}$ alkyl which may be substituted.

The acyl group for $N^\alpha$-acylamino acid (X) includes carboxylic acid acyls such as alkanoyl, benzoyl and arylalkanoyl. These acyl groups may have at least one substituent (e.g. halogen, $C_{1-3}$ alkyl, $C_{1-3}$ alkoxy, nitro). Examples of the alkanoyl include $C_{1-3}$ alkanoyls such as formyl, acetyl, propionyl and chloroacetyl. Examples of the benzoyl include benzoyl and p-chlorobenzoyl.

Examples of the arylalkanoyl include phenyl-$C_{1-3}$ alkanoyls such as phenylacetyl and phenylpropionyl.

Further as for formula (I), R may be $C_{1-6}$ alkyl which is straight-chain alkyl or branched, $C_{1-3}$ alkyl which is substituted with hydroxy, $C_{1-3}$ alkylthio, thiol, phenyl, hydroxyphenyl or indolyl, or $C_{1-4}$ alkyl which is substituted with amino, carboxyl, guanidyl or imidazolyl.

Acylamino acid racemase-producing microorganisms can be found by the procedure discussed below, for instance. Microorganisms isolated from natural sources or microorganisms available from a depository institute are cultivated by a standard method (a compound which induces said enzyme or which promotes the production of said enzyme, e.g. a substrate for said enzyme or metal salt, is added to the medium as needed); cells are harvested from each obtained culture; the cells, after being washed with a buffer, etc. if necessary, are suspended in a phosphate-buffer solution (pH7) containing appropriate amounts of N-acetyl-D-methionine and magnesium sulfate; the suspension is shaken at 30° C. for one night to cause reaction. After cell removal from the reaction broth, given amounts of L-aminoacylase and, if necessary, cobalt chloride are added to the supernatant, and reaction is carried out at 37° C. for several hours, whereafter the reaction mixture is applied to TLC (n-butanol:acetic acid:-water=3:1:1). The reaction broths which exhibit a methionine spot by Ninhydrin reaction are selected, after which they are assayed for the amount of methionine by Ninhydrin reaction and/or high performance liquid chromatography. To the methionine-positive reaction broths, D-amino acid oxidase solution is added, and reaction is carried out at 30° C. for 20 hours to decompose the D-methionine, whereafter each reaction mixture is again applied to Ninhydrin reaction, high performance liquid chromatography and/or bioassay using *Pediococcus acidilacti* ATCC 8042 [J. Biol. Chem., 177, 533 (1949)], to determine the residual methionine, i.e. L-methionine in the reaction mixture. The strains which have given L-methionine in a reaction broth are capable of producing L-methionine from N-acetyl-D-methionine; these strains must produce acylamino acid racemase and/or amino acid racemase.

The L-methionine-positive strains are then again cultivated using the same conditions as above and cell suspensions are prepared. To each suspension, L-methionine, in place of N-acetyl-D-methionine, is added, and reaction is carried out in the same manner as above. After cell removal, the reaction mixture is assayed for the amount of D-methionine by a colorimetric method using D-amino acid oxidase, peroxidase, phenol and 4-aminoantipyrine [Clin. Chem., 20, 470 (1974)], and the D-methionine-negative strains are selected.

Another D-$N^\alpha$-acylamino acid may be used in place of N-acetyl-D-methionine as used here. Acylamino acid racemase-producing microorganisms can be obtained by thus selecting strains which do not exhibit amino acid racemase activities and which produce from D-$N^\alpha$-acylamino acid the corresponding L-$\alpha$-amino acid.

The N-acylamino acid racemase-producing microorganisms which have been found by this method are listed in Table 1.

TABLE 1

| Acylamino Acid Racemase-producing microorganism | Production of L-methionine from N-acetyl-D-methionine (25 mM) | Production of D-methionine from L-methionine (25 mM) |
|---|---|---|
| Streptomyces sp. Y-53 (FERM P-9518) | 12.7 mM | 0 mM |
| Actinomadura roseoviolacea (IFO 14098) | 1.2 | 0 |
| Actinomyces aureomonopodiales (IFO 13020) | 1.6 | 0 |
| Jensenia canicruria (IFO 13914) | 2.1 | 0 |
| Amycolatopsis orientalis (IFO 12806) | 1.4 | 0 |
| Sebekia benihana (IFO 14309) | 3.9 | 0 |
| Streptomyces coelescens (IFO 13378) | 4.2 | 0 |
| Streptomyces celluloflavus (IFO 13780) | 3.2 | 0 |
| Streptomyces alboflavus (IFO 13196) | 2.9 | 0 |
| Streptomyces aureocirculatus (IFO 13018) | 2.3 | 0 |
| Streptomyces diastatochromogenes (IFO 13389) | 1.8 | 0 |
| Streptomyces spectabilis (IFO 13424) | 2.8 | 0 |
| Streptomyces tuirus (IFO 13418) | 3.8 | 0 |
| Streptomyces griseoaurantiacus (IFO 13381) | 2.7 | 0 |

Although the acylamino acid racemase-producing microorganisms listed in Table 1 unexpectedly belong to the actinomycetes, any microorganism, whether it belongs to the actinomycetes, bacteria, fungi, yeasts or mushrooms, can be used for the present invention, as long as it is an acylamino acid racemase-producing microorganism as determined by the above method.

The microbiological characteristics of any acylamino acid racemase-producing microorganism isolated from soil at Arashiyama, Kyoto, Japan (listed in Table 1 as Streptomyces sp. Y-53) are as shown below.

(a) Morphology

The spore-bearing hyphae exhibit monopodially branching, and form hooks, loops or rarely primitive spirals (2 or 3 turns) [Retinaculum-Apertun(RA)]. The mature spore chains have more than 10 spores per chain and the spore shows a cylindrical form (0.7 to 0.9 × 1.1 to 1.5 μm) with smooth surface. Motile elements, special organs or structures are not obserbed. This strain has LL-diaminopimeric acid as a cell wall component and has no characteristic sugar (the cell wall type I).

(b) Cultural characteristics

Cultural characteristics of Y-53 strain on various media are shown in Table 2. Colors represented in Table 2 are determined by comparing them with color chips of the "Color Harmony Manual", 4th edition, Container Corporation of America.

TABLE 2

| | | Cultural Characteristics on Various Media | | |
|---|---|---|---|---|
| Medium | Growth | Color of Aerial Mycelium | Color of substrate mycelium (reverse Color) | Diffusible Pigment into the Medium |
| (1) Sucrose-nitrate agar | Poor | Silver Gray (3fe) | Covert Gray (2fe) | None |

TABLE 2-continued

| Medium | Growth | Color of Aerial Mycelium | Color of substrate mycelium (reverse Color) | Diffusible Pigment into the Medium |
|---|---|---|---|---|
| (2) Gluscose-asparagine agar | Good | Gray (d) | Covert Brown (2li) to DK Brown (3nl) | Brown |
| (3) Glycerine-asparagine agar | Medium | Lt Gray (c) to Gray (d) | Slate Tan (2ig) | Faint brown |
| (4) Inorganic salts-starch agar | Good | Covert Gray (2fe) | Mustard Tan (2lg) to Covert Brown (2nl) | Faint brown |
| (5) Tyrosine agar | Good | Lt Gray (c) | DK Brown (3nl) | Chestnut Brown (4ni) |
| (6) Nutrient agar | Good | None | Lt Ivory (2ca) | None |
| (7) Yeast extract-malt extract agar | Good | Covert Gray (2fe) | DK Brown (2pn) | DK Brown (2pn) |
| (8) Oatmeal agar | Medium | Covert Gray (2fe) | Covert Tan (2ge) to Slate Tan (2ig) | Faint brown |

(c) Physiological characteristics

① Temperature range for growth: From 14° to 37° C. (optimum temperature for growth: 20° to 30° C.), on yeast extact-malt extract agar ② Gelatine liquefaction: Positive ③ Starch hydrolysis: Positive ④ Defatted milk coagulation: Negative Defatted milk peptonization: Positive ⑤ Melanoid formation: Negative (d) Utilization of Carbon source Positive: Glucose, xylose, rhamnose Doubtful: Fructose Negative: Arabinose, sucrose, raffinose, mannitol, inositol From the above microbiological characteristics, Y-53 strain was identified as a strain belonging to the genus Streptomyces; the present inventors named this strain Streptomyces sp. Y-53. The strain Y-53 has been deposited at the Institute for Fermentation, Osaka under accession number IFO-14596, and has also been deposited at the Fermentation Research Institute, Agency of Industrial Science and Technology, Ministry of International Trade and Industry, Japan under accession number FERM-P9518 since Aug. 13, 1987, the deposit being converted to a deposit under the Budapest Treaty, has been stored at FRI under the accession number of FERM BP-1889.

Note that there can be used for the present invention any of the mutants and zygotes derived from Y-53 mentioned above or another acylamino acid racemase-producing microorganism listed in Table 1 by means of cell fusion techniques or of the transformants obtained by inserting into an appropriate host microorganism a part (containing the acylamino acid racemase-encoding region) of the genes of these strains, as long as it produces acylamino acid racemase.

The medium for the cultivation of the above-mentioned microorganisms may be a liquid or a solid, as long as it contains nutrient sources utilizable by the relevant strain and promotes acylamino acid racemase production. For mass cultivation, a liquid medium is convenient.

For the medium, substances that can be used are those which are generally used to cultivate microorganisms, such as carbon sources, nitrogen sources and inorganic nutrients. Glucose, glycerine, dextrin, starch, molasses and animal and vegetable oils, for instance, may serve as carbon sources. Soybean meal, corn steep liquor, cotton seed meal, meat extract, peptone, yeast extract, ammonium sulfate, sodium nitrate and urea, for instance, may serve as nitrogen sources. Sodium salts, potassium salts, calcium salts, magnesium salts, manganese salts, iron salts, cobalt salts, zinc salts, phosphate salts and other salts may further be added, if necessary.

Cultivation can be conducted by stationary culture, shaking culture or aerobic submerged culture. Aerobic submerged culture is preferred for mass treatment. Cultivation temperature can be in the range of 15° to 37° C., preferably 20° to 37° C. The medium is preferably maintained at a pH in the range 5 to 9. Cultivation is carried out for 18 hours to 4 days and is stopped when the amount of accumulated acylamino acid racemase has reached the maximum.

For harvesting acylamino acid racemase from the culture, the culture is first fractionated into the cells and culture filtrate by centrifugation or another procedure, and, when said enzyme is present in the cells, the cells are disrupted by various methods of cell disruption such as lytic enzyme treatment, ultrasonication, French press treatment and Dyno-Mill treatment as used singly or in combination to thereby solubilize the enzyme. When said enzyme is present in the culture filtrate, the culture filtrate may be subjected directly to the next purification process.

For the purification of said enzyme as solubilized or as present in the culture filtrate, appropriate combinations of known enzyme purification methods can be used, for instance, the salting-out methods utilizing ammonium sulfate, etc., anion exchange chromatography utilizing diethylaminoethyl cellulose, etc., cation exchange chromatography utilizing carboxymethyl cellulose, etc., gel filtrations utilizing dextran gel, etc., hydrophobic chromatography utilizing a hydrophobic resin and affinity chromatography, whereby acylamino acid racemase standard samples can be obtained with a degree of purification as appropriate for the purpose.

The acylamino acid racemase obtained by this invention has the physicochemical characteristics described below.

① Action

Said enzyme acts on L-$N^\alpha$-acylamino acid to convert it to the corresponding D-$N^\alpha$-acylamino acid, and acts on the D-$N^\alpha$-acylamino acid to convert it to the corresponding L-$N^\alpha$-acylamino acid. That is, the enzyme catalyzes the reversible reaction shown by the following formula:

$$\text{L-}N^\alpha\text{-acylamino acid} \rightleftharpoons \text{D-}N^\alpha\text{-acylamino acid}$$

② Substrate specificity

As shown in Table 3 below, the enzyme acts on optically active $N^\alpha$-acylamino acids but does not act on the corresponding optically active $\alpha$-amino acids.

Note that the relative activities in Table 3, where N$^\alpha$-acylamino acids were used as substrates, were determined by the method of enzyme activity determination described in the term ③, with the values representing the found amount (mM) of the produced α-amino acids corresponding to respective substrates as calculated on the basis of the amount of produced methionine taken as 100. When the substrate was an L-N$^\alpha$-acylamino acid, D-aminoacylase as produced by Y-53 strain was used in place of L-aminoacylase. When the substrate was an optically active amino acid, the reaction broth, after treatment with D- or L-amino acid oxidase (both produced by Sigma Co.), was subjected to high performance liquid chromatography to confirm whether the optical enantiomer of the substrate had been formed.

TABLE 3

| Substrate | Relative Activity | Substrate | Relative Activity |
| --- | --- | --- | --- |
| N-acetyl-D-methionine | 100 | N-acetyl-L-methionine | 100 |
| N-formyl-D-methionine | 40 | N-formyl-L-methionine | 63 |
| N-acetyl-D-alanine | 33 | N-acetyl-L-alanine | 21 |
| N-benzoyl-D-alanine | 14 | N-benzoyl-L-alanine | ND |
| N-acetyl-D-leucine | 37 | N-acetyl-L-leucine | 74 |
| N-acetyl-D-phenylalanine | 64 | N-acetyl-L-phenylalanine | 84 |
| N-chloroacetyl-D-phenylalanine | 90 | N-chloroacetyl-L-phenylalanine | 112 |
| N-acetyl-D-tryptophan | 10 | N-acetyl-L-tryptophan | 8 |
| N-acetyl-D-valine | 35 | N-acetyl-L-valine | 19 |
| N-chloroacetyl-D-valine | 80 | N-chloroacetyl-L-valine | 105 |
| N-acetyl-D-allo-isoleucine | 33 | N-acetyl-L-allo-isoleucine | ND |
| D-methionine | 0 | L-methionine | 0 |
| D-alanine | 0 | L-alanine | 0 |
| D-leucine | 0 | L-leucine | 0 |
| D-phenylalanine | 0 | L-phenylalanine | 0 |
| D-tryptophan | 0 | L-tryptophan | 0 |
| D-valine | 0 | L-valine | 0 |

ND: Not determined.

③ Method of enzyme activity determination

Acylamino acid racemase catalyzes the reversible reaction. That is, when a D-N$^\alpha$-acylamino acid is used as the substrate, the L-N$^\alpha$-acylamino acid produced and accumulated with the progress of the reaction becomes another substrate for said enzyme, and it is thus also subjected to the action of the enzyme and converted to the D-N$^\alpha$-acylamino acid, i.e. the substrate. For the determination of the true reaction rate, it is necessary to immediately convert the reaction product to other compounds and exclude them from the reaction system.

For this purpose, the present inventors added an excessive amount of, when the product was L- or-D-N$^\alpha$-acylamino acid, L-or D-aminoacylase to the reaction system to determine the enzyme's activity to thereby allow the deacylation reaction for the product to proceed simultaneously, and determined the amount of eventually accumulated L- or D-amino acid, this value (μM) being regarded as equal to the amount of produced L- or D-N$^\alpha$-acylamino acid.

Enzyme activities are determined by means of a mixed reaction system comprising 50 μl of a solution of the enzyme, 40 μl of a solution of the substrate, 10 μl of an L-aminoacylase solution and 400 μl of a 50 mM Tris-HCl buffer (pH 7.5). As the enzyme solution, a solution prepared by dissolving an acylamino acid racemase standard sample in a Tris-HCl buffer (pH 7.5) to 1 to 0.2 unit/ml was used; as the L-aminoacylase solution, a solution prepared by dissolving an L-aminoacylase standard sample (a commercially available product such as that produced by Sigma Co. may be used, but the L-aminoacylase extracted and purified from Y-53 strain was used in the present invention) in a Tris-HCl buffer (pH 7.5) to 40 to to 8 units/ml.

The above solutions are mixed together by the sequential addition of the Tris-HCl buffer, substrate solution, L-aminoacylase solution and enzyme solution in this order, and reaction is initiated at 30° C. simultaneously with the addition of the enzyme solution. The reaction is continued for 120 minutes when the enzyme solution's activity is low, or for 10 minutes when the activity is high, and the reaction is terminated by 3 minutes of heat treatment at 100° C.

For the determination of enzyme activities, the amount of methionine produced in the reaction system is determined by high performance liquid chromatography, and the enzyme activity corresponding to the production of 1 μmol/min. methionine is expressed as 1 unit. When a ymM concentration of methionine has been produced in the reaction system during a reaction time of x minutes, the activity (αunit) of the enzyme in 50 μl solution is calculated by the following equation:

$$\alpha = \frac{y}{2x}$$

④ Optimum pH for enzyme activity and pH range for enzyme stability

Figure 1:
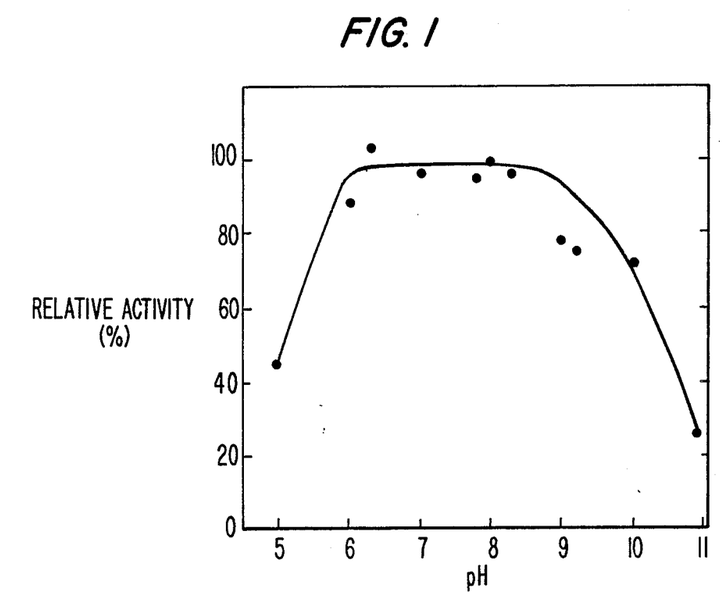
FIG. 1 shows the pH dependency of acylamino acid recemase.
Figure 2:
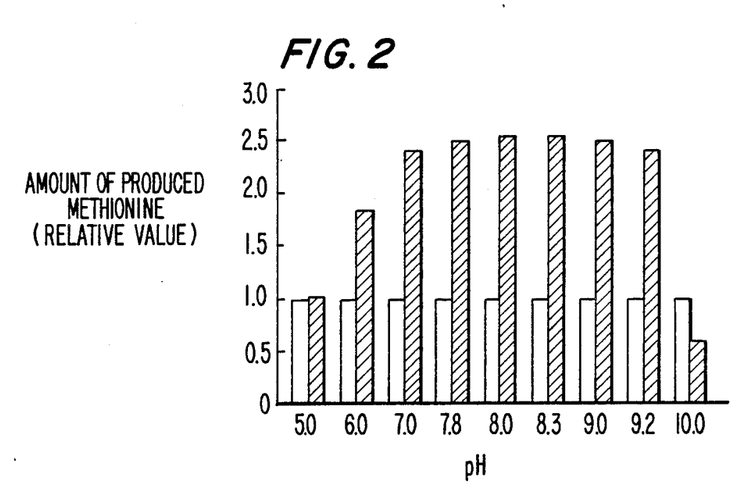
FIG. 2 shows the amounts of methionine produced by means of acylamino acid recemase at various pH values as expressed in relative values for the amounts with the 4-hour reaction (▨) as calculated on the basis of the amounts with the 2-hour reaction (▭) as taken as 1.

Reaction was carried out for 2 or 4 hours by the method of enzyme activity determination decribed above, but sodium acetate-HCl buffers (pH 4.0, 5.0), potassium primary phosphate-sodium secondary phosphate buffers (pH 6.0, 7.0, 8.0) potassium primary phosphate-sodium borate (pH 6.3, 7.8, 8.3, 9.0) and sodium carbonate-sodium borate (pH 9.2, 10.0, 10.9,) were each used in place of the Tris-HCl buffer (pH 7.5) and the relative activity in each solution was calulated from the ratio of the amount of produced methionine.

FIG. 1 shows the relative enzyme activities in the solutions of respective pH values when reaction was continued for 2 hours; it is known from FIG. 1 that the optimum pH is about 8.

FIG. 2 shows the degrees of increases in the amounts of produced methionine when reaction time was extended from 2 hours to 4 hours. It can be said that the enzyme is stable under the conditions that the 4-hour reaction gave methionine in an amount nearly 2 times that obtained in the 2-hour reaction. From FIG. 2, it is known that acylamino acid racemase is stable between pH 6 and 9.

⑤ Range of suitable temperature for the action

Figure 3:
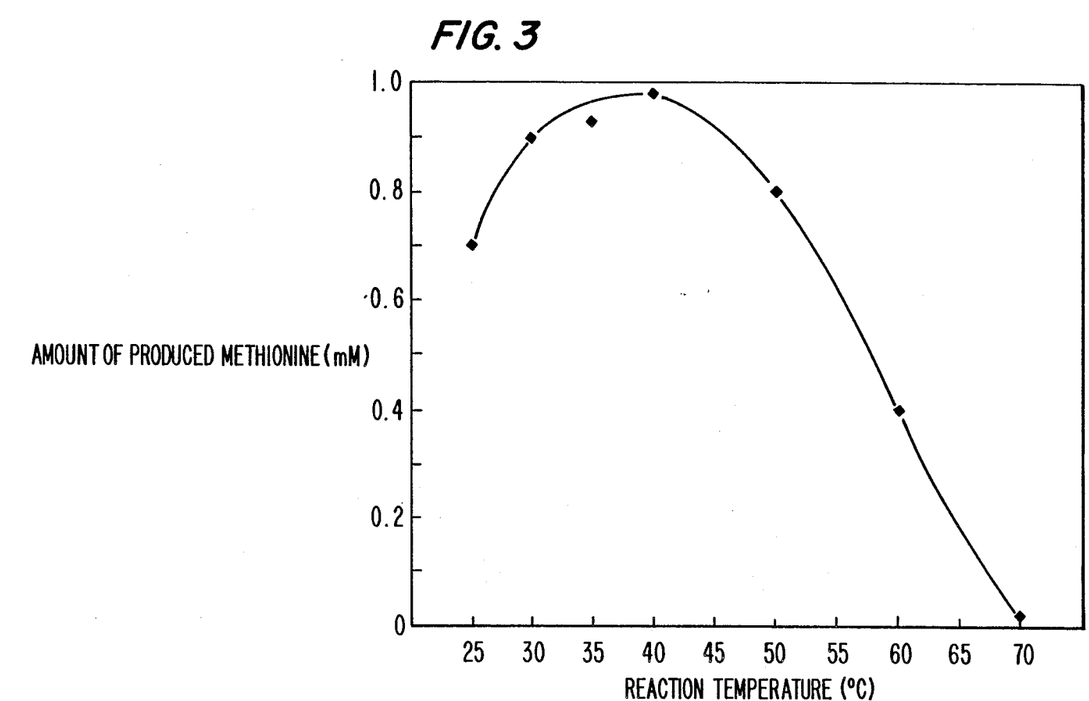
FIG. 3 shows the relationship between reaction temperature and enzyme activity in acylamino acid recemase.

The amount of L-methionine produced from N-acyl-D-methnionine was determined with the reaction temperature (30° C.) in the standard method of enzyme activity determination (described in the term ③) varied to 25, 30, 35, 40, 50, 60 or 70°C. The amount of the enzyme used was increased, and reaction time was 5 minutes. The obtained results are shown in FIG. 3. As is evident from FIG. 3, the range of suitable temperature for the action is from 30° to 50° C.

⑥ Influence of various temperature on enzyme activity

Figure 4:
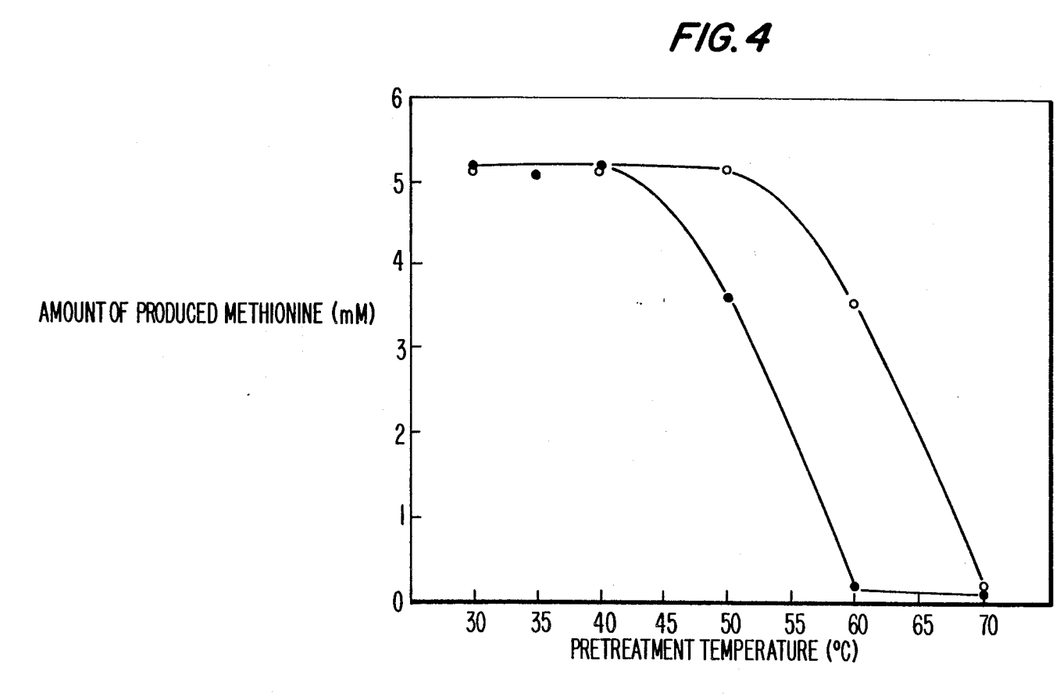
FIG. 4 shows the heat stability of acylamino acid recemase.

The enzyme solution, after 30 minutes of heat treatment at 30, 35, 40, 50, 60 or 70° C., was assayed for residual activity by the standard method of activity determination. The results are shown on the black-dotted curve in FIG. 4.

As is evident from this curve, the enzyme is stable below 40° C. but inactivates above 50° C. Separately, heat treatment was conducted using the same conditions as above but 1 mM cobalt ions were added to the enzyme solution, and the residual activity was determined; the results obtained were different from those obtained under the $Co^{++}$-free conditions. The results obtained with the presence of added $Co^{++}$ are shown on the white-dotted curve in FIG. 4; it is known that the enzyme, in the presence of $Co^{++}$, is stable below 50° C. and inactivates at 60° C.

⑦ Influences of metal ions

Using metal salt-free solutions as controls, reaction was carried out by the method of enzyme activity determination described in the term ③, but the 12.5 mM (final concentration in the reaction mixture: 1 mM) cobalt chloride added to the substrate solution was excluded and, in place thereof, 12.5 mM or 125 mM (final concentration in the reaction mixture is 1 mM or 10 mM, respectively) of various metal salts or EDTA was added, and the influences of the metal ions on the enzyme activities were examined. Note that it had been confirmed that the activities of the L-aminoacylase used in this experiment are not affected by these additives. The results are shown, in Table 4. In Table 4, the enzyme activities are presented in relative activities on the basis of the values obtained in the case of no additives as taken as 100.

TABLE 4

| Influences of Metal Ions on Enzyme Activites | | |
|---|---|---|
| | Additive Concentration | |
| Additive | 1 mM | 10 mM |
| None | 100 | 100 |
| LiCl | 100 | 120 |
| NaCl | 100 | 130 |
| KCl | 110 | 130 |
| $MgSO_4.7H_2O$ | 890 | 1350 |
| $CaCl_2$ | 95 | 100 |
| $SrCl_2.6H_2O$ | 94 | 110 |
| $BaCl_2.2H_2O$ | 85 | 120 |
| $Al_2(SO_4)_3.16H_2O$ | 79 | 0 |
| $CrCl_3.6H_2O$ | 96 | 100 |
| $MnSO_4.7H_2O$ | 780 | 1050 |
| $FeSO_4.7H_2O$ | 100 | 560 |
| $CoCl_2.6H_2O$ | 2100 | 140 |
| $NiSO_4.6H_2O$ | 460 | 0 |
| $CuSO_4.5H_2O$ | 0 | 0 |
| $ZnSO_4.7H_2O$ | 810 | 80 |
| $NaMoO_4.2H_2O$ | 96 | 0 |

TABLE 4-continued

| Influences of Metal Ions on Enzyme Activites | | |
|---|---|---|
| | Additive Concentration | |
| Additive | 1 mM | 10 mM |
| $SnSO_4$ | 92 | 100 |
| $PbCl_2$ | 78 | 100 |
| EDTA | 68 | 0 |

As shown in Table 4, said enzyme is noticeably activated in certain limited ranges of concentrations of several kinds of metal ions. That is, cobalt ions have a noticeable activating effect at low concentrations (around 1 mM), but hardly activate the enzyme at 10 mM. Zinc ions and nickel ions have a similar tendency. In the case of magnesium ions, the activating effect is greater at 10 mM than at 1 mM. Manganese ions and bivalent iron ions have a similar tendency. Of the examined kinds of metal ions, copper ions showed a noticeable inhibitory effect. Aluminum ions and molybdic ions also inhibit the enzyme activity at 10 mM. EDTA has a noticeable inhibitory effect at 10 mM.

⑧ Molecular weight

About 200,000: The molecular weight of the enzyme which was obtained in the step 5 in Table 5 in Example 2 was measured by the polyacrylamide gel electrophoresis according to the method of Davis [Ann. N.Y. Acad. Sci., 121, 404 (1964)] under the following conditions: the polyacrylamide gradient gel, PAG plate 4/15, produced by Daiichi Pure Chemicals, Co., Japan; 30mA (constant current) for 2 hours. The molecular weight of the enzyme was estimated on the basis of comparison of mobility between the sample enzyme and the standard proteins.

The molecular weight of the subunit of this enzyme was measured by the same method using the SDS-PAG plate 4/20 (Daiichi Pure Chemicals, Co., Japan) in the presence of sodium dodecyl sulfate (SDS) under the same conditions. The molecular weight of the subunit was estimated as about 40,000.

⑨ Isoelectric point 4.8 (Determined by agarose electrophoresis with the carrier ampholite. For the determination, electrophoresis was conducted at a constant power supply (2 W) for 2.5 hours using the electrophoresis unit (model 2117 Multiphor II,LKB) and Pharmalyte, pH 3 to 10 (Pharmacia, Sweden).

The acylamino acid racemase of the present invention, when used in combination with L-aminoacylase or D-aminoacylase, enables the production in one step of optically active L-α-amino acid or optically active D-α-amino acid from inexpensive DL-N$^α$-acylamino acid.

L-aminoacylase is easily obtainable by a known method, but a commercially available product may also be used. D-aminoacylase is reported to be produced by bacteria of the genus Streptomyces [Japanese published unexamined patent application Nos. 126969/1987 and 126976/1987], the genus Pseudomonas [Nature, 170,888 (1952), Japanese published examined patent application No. 31477/1985] and the genus Alcaligenes [Proceedings of the annual meeting of the Agricultural Chemical Society of Japan, 1987, p. 659]. In addition, most of the strains isolated as acylamino acid recemase-producing microorganisms in the present invention produce not only acylamino acid recemase but also D-aminoacylase and/or L-aminoacylase.

Therefore, for the production of an optically active α-amino acid from DL-N$^\alpha$-acylamino acid as the starting material, a standard sample which is appropriate for the purpose and manner of use is chosen from the acylamino acid recemase standard samples with various degrees of purification as produced by the method of this invention. When an L-α-amino acid is to be produced, for instance, the chosen standard enzyme sample and L-amino-acylase which is commercially available or separated from an appropriate L-aminoacylase-producing microorganism are in combination or alternately reacted with DL-N$^\alpha$-acylamino acid. When virtually 100% of the starting material has been converted to L-α-amino acid, the reaction is stopped and the desired L-α-amino acid is recovered from the reaction mixture.

Here, the standard sample which is appropriate must meet the requirement that, when the purpose of its use is to produce L-amino acid, D-aminoacylase is not contained in the standard sample. In cases where the enzyme is immobilized for the use as a bioreactor, the standard sample may be either of cells containing the enzyme themselves and cell-free extract in the case of the entrapping immobilization method, while the degree of purification of the standard enzyme sample must be slightly higher in the case of the ion exchange resin adsorption method or insoluble carrier covalent bond method.

Acylamino acid recemase standard samples which can be used for the production method for optically active amino acids according to the present invention include, when the acylamino acid racemase-producing micro-organism produces neither L-aminoacylase nor D-aminoacylase, the cultured cells of the microorganism, processing products thereof and standard samples extracted and purified to various degrees from the cells.

When producing L-aminoacylase or D-aminoacylase as well, the acylamino acid recemase-producing microorganism can be used to produce L-α-amino acid or D-α-amino acid in exactly the same manner as with the above-mentioned microorganism. In this case, it is not necessary to separately add L-aminoacylase or D-aminoacylase when the activity of the coproduced L-aminoacylase or D-aminoacylase is by far stronger than that of the acylamino acid recemase.

When the acylamino acid racemase-producing microorganism produces both L-aminoacylase and D-aminoacylase as well, a strain lacking D-aminoacylase or L-aminoacylase may be mutationally induced by a routine method to produce L-amino acid or D-amino acid, respectively. Processing products at various purification levels, ranging from cultured cells to standard enzyme samples, can also be used as appropriate.

Note that the processing product, when it is at the level of cultured cell or cell-free extract, may contain an enzyme which decomposes the desired amino acid; in this case, the amino acid decomposing activity must be deleted or eliminated. When the microorganism is not an aminoacylase-deficient strain, it is diffucult to use it at the cell level directly to produce optically active α-amino acid, but the microorganism can be used after inactivation of one or both of the aminoacylases without affecting the acylamino acid recemase by means of heat treatment or addition of inhibitors, etc. For the preparation of a standard sample of acylamino acid racemase from a strain which coproduces both L- and D-aminoacylases, acylamino acid racemase is first extracted from cultured cells, whereafter the aminoacylases interfering with the production of the desired amino acid are separated and removed, and, if necessary, an appropriate procedure of purification is further added, whereby the standard sample is prepared.

When an L- or D-α-amino acid is produced by means of acylamino acid racemase and L- or D-aminoacylase, there normally are used such methods as (1) the method in which a standard sample of acylamino acid racemase and L- or D-aminoacylase are dissolved in a buffer at pH 6 to 9 containing appropriate amounts of the starting material DL-N$^\alpha$-acylamino acid and Co$^{++}$ or other kind of metal ions, this solution being kept standing at an appropriate temperature until the completion of the reaction; (2) the method in which a standard sample of acylamino acid recemase and L- or D-aminoacylase are immobilized together or separately by a known method, after which they are filled in one or more stages in a reaction vessel to thereby prepare a bioreactor, and a buffer at pH 6 to 9 containing DL-N$^\alpha$-acylamino acid and Co$^{++}$ or other kind of metal ions is passed through this reactor to cause reaction; and (3) the method in which both enzymes are dissolved in one of the compartments of a reaction vessel, divided into 2 compartments by a ultrafiltration membrane, a solution of the starting material is added for the reaction, and the product which has passed the ultrafiltration membrane is recovered. In any case, it is desirable that the reaction mixture is sterilized and handled as aseptically as possible.

Since the final reaction mixture thus obtained contains nothing but the organic acid which has been produced by hydrolysis of the desired optically active amino acid and acyl groups, the desired amino acid can easily be recovered by a conventional method.

EXAMPLES

Example 1

A medium (pH 7.0) containing BBL Trypticase soy broth (available from Becton Dickinson Co.) and 0.1% N-acetyl-D-methionine was dispensed in 20 ml portions into 200 ml Erlenmeyer flasks and sterilized at 120° C. for 20 minutes. Separately, Streptomyces sp. Y-53 strain, after cultivation by liquid culture, was stored under freezing conditions (−80° C.), and used in solution as a seed inoculum as necessary.

To 30 flasks of the above medium, the frozen microorganism, in solution, was aseptically inoculated in an amount of 0.7 ml per flask, and this was followed by 2 days of shaking culture at 28° C. to create seed cultures. Each seed culture was then transferred to 500 flasks of the same medium in an amount of 1 ml per flask, and subjected to 42 hours of shaking culture at 28° C. The contents of the flasks were collected, and cells were collected by centrifugation (4° C., 10,000 rpm, 15 minutes). The cells were washed with a physiological saline, and 216 g of wet cells were obtained. The following procedures were all performed at a low temperature below 4° C.

The 216 g of wet cells was suspended in 1 l of a 50 mM phosphate buffer (pH 7.0) and applied to the Dyno-Mill (cell disruptor produced by Willy A. Bachofen AG) to thereby disrupt the cells. The glass beads used had a diameter of 0.1 to 0.2 mm, and the flow rate was 60 ml/min. The processed liquid was centrifuged at 4° C., 10,000 rpm for 20 minutes to create 1700 ml of a cell-free extract. The acylamino acid racemase activity of this extract was 4.9 units, and the specific activity was 0.52 milliunit/mg protein. The total protein amount was determined by the Bio-Rad protein assay method.

Example 2

To the 1700 ml of cell-free extract obtained in Example 1, 300 g of ammonium sulfate was added little by little while cooling and stirring the extract. After addition of the entire amount, agitation was continued for another 30 more minutes, and the mixture was centrifuged at 4° C., 10,000 rpm for 30 minutes to give 1660 ml of clear supernatant.

The 1660 ml of supernatant was adsorbed to a column (4.8 cm ×30 cm) of TSKHW65C (Tosoh Co., Japan) equilibrated with a 50 mM phosphate buffer (pH 7.0, containing 30% saturated ammonium sulfate), and the column was washed with 1000 ml of the above phosphate buffer, whereafter the protein component was eluted with a phosphate buffer containing no ammonium sulfate, and the eluate fraction showing an activity of the desired enzyme was collected. To 330 ml of the active fraction thus obtained, 128 g of ammonium sulfate was added little by little while cooling and stirring the fraction. The resulting precipitate was collected by centrifugation at 10,000 rpm for 30 minutes. This precipitate was dissolved in 50 ml of a 50 mM phosphate buffer (pH 7.0) and desalted through a Sephadex G25 column (Pharmacia, Sweden). The crude enzyme solution thus obtained was adsorbed to a column (4.8 cm ×30 cm) of DEAE Toyopearl 650M (Tosoh Co., Japan) equilibrated with a 50 mM phosphate buffer. The column was washed with 1000 ml of the same buffer, after which it was eluted with the same buffer as containing 0.2 M NaCl to give 340 ml of an active fraction. To this active fraction, 133 g of ammonium sulfate was added by a routine method. The resulting precipitate was collected by centrifugation (4° C., 10,000 rpm, 30 minutes) and dissolved in 30 ml of the same buffer. This solution was desalted through a column of Sephadex G5, and 59 ml of a crude enzyme solution was obtained. This crude enzyme solution was adsorbed to a DEAE-5PW column (Tosoh Co. Japan, 2.15 cm dia. ×15 cm) equilibrated with the same buffer, and applied to preparative high performance liquid chromatography (model HLC-837, Tosoh Co. Japan), and elution was conducted with a linearly increased concentration of NaCl from 0 to 0.5 M. The elution rate was 4 ml per min. The fraction which eluted at 32 to 36 minutes was recovered to obtain 16 ml of an active fraction. The acylamino acid recemase activity in this fraction was about 7.2 units, and the specific activity was about 63 milliunit/mg protein. The specific activity increased to about 122 times that of the cell-free extract.

This active fraction was further applied to a TSK-G3000SW column (Tosoh Co. Japan, 5.5 cm dia. ×60 cm) equilibrated with a 50 mM phosphate buffer, and gel filtration was conducted at a flow rate of 1 ml per min., and the active fraction was separately taken. Since this fraction exhibited a single band in polyacrylamide gel electrophoresis, it was judged that the acylamino acid racemase had been almost purified. This fraction contained 1.2 units of acylamino acid racemase activity with a specific activity of 2.8 units/mg protein.

The total activities of acylamino acid racemase, contents of total protein and specific activities in respective processes of fraction as well as the volumes of respective sample solution, are shown in Table 5.

TABLE 5

Purification of the Enzyme

| Procedure | Volume (ml) | Total Activity (U) | Total Protein (mg) | Specific Activity (mU/mg) |
|---|---|---|---|---|
| Cell-free extract | 1700 | 4.86 | 9699 | 0.52 |
| HW 65C column | 330 | 3.43 | 1617 | 2.0 |
| DEAE Toyopearl column | 59 | 4.75 | 708 | 6.7 |
| DEAE 5PW column | 16 | 7.22 | 113 | 63.5 |
| G3000SW column | 8 | 1.23 | 0.43 | 2870 |

Example 3

In the same manner as in Example 1, Streptomyces sp. Y-53 strain was cultivated in 10 liters of the medium. Cells obtained by the 42-hour cultivation were collected and washed once with a 0.8% NaCl solution to obtain 300 g of wet cells.

The wet cells were disrupted by means of Dyno-Mill (a cell disruptor) in the same manner as in Example 1, and centrifugation (10,000 rpm, 20 minutes) was conducted to obtain 1680 ml of a supernatant. This supernatant contained 21 units of acylamino acid racemase, 315 units of L-aminoacylase and 75 units of D-aminoacylase. To this supernatant, ammonium sulfate was added to give 30% saturation, and the resulting precipitate was centrifugally removed. To the centrifugal supernatant fraction, ammonium sulfate was further added to give 60% of the saturation, and the resulting precipitate was recovered by centrifugation. The obtained precipitate was dissolved in a 50 mM phosphate buffer (pH 7.0) and desalted by gel filtration using Sephadex G25 equilibrated with the same buffer. The obtained solution was subjected to ion exchange chromatography.

A DEAE Toyopearl 650M column (resin volume: 700 ml) equilibrated with a 50 mM phosphate buffer (pH 7.0) was charged with the above desalted solution(490 ml), and washed with 2 l of the phosphate buffer to thereby wash out the non-adsorbable components. From this washing, 114 units of D-aminoacylase was recovered. This DEAE Toyopearl 650M column has acylamino acid racemase (about 20 units) and L-aminoacylase (about 900 units) being relatively strongly adsorbed thereto, and they will not be eluted unless a solution containing more than 0.2 moles of salts is flowed through the column.

While maintaining the above column at 30° C., a 20 mM phosphate buffer containing 0.5% N-acetyl-DL-methionine and 1 mM cobalt chloride was flowed through the column at a flow rate of 30 ml per hour. 3 l of the effluent was collected and passed through IR 120 cation exchange resin, after which it was concentrated under reduced pressure until it was dry and solid. The obtained residue, after being washed twice with 10 ml of cool absolute alcohol, was dissolved in about 100 ml of hot water, and the crystal which separated during cooling was collected by filtration. Furthermore, alcohol was added drop-by-drop to the filtrate, and this mixture was kept standing overnight. The crystal which separated was collected and dried to obtain 9.6 g of L-methionine. The melting point was 280° to 281° C., $[\alpha]_D^{25} -8.2°(c=1\%)$. This product showed entirely the same behaviors as those of a standard sample of L-methionine in high performance liquid chromatography and thin layer chromatography. In addition, this product, when melted together with a standard sample, exhibited no drop of melting point.

Example 4

To a 20ml-seed culture medium consisting of 1.5% glycerine, 1.0% peptone, 1.0% yeast extract, 0.5% NaCl, 0.25% $K_2HPO_4$, 0.25% $MgSO_4.7H_2O$ and 0.05% N-acetyl-DL-methionine (pH 7.0) in a 200 ml-Erlenmeyer flask, a 0.7 ml-stock culture prepared in Example 1 was inoculated and cultivated on a rotary shaker (200 rpm) at 28° C. for 18 hours. One milliliter of the resultant culture was transferred to a 200 ml-Erlenmeyer flask containing 25 ml of production medium consisting of 0.5% glycerine, 1.0% peptone, 0.5% NaCl, 0.25% $K_2HPO_4$ and 0.05% N-acetyl-DL-methionine(pH 7.0). Cultivation was carried out under the same conditions mentioned above. The following procedures were performed at 0° to 4° C.

Cells from 5 liters of cultured broth were harvested by centrifugation (10,000 rpm, 15 min) and were washed with a 0.85% NaCl aqueous solution. The washed cells (385 g, wet weight) were suspended in one liter of 50 mM phosphate buffer (pH 7.0) and disrupted by Dyno-Mill (Willy A. Bachofen AG) under the following conditions: the size of diameter of glass beads, 0.1 to 0.2 mm; flow rate of the cell suspension, 60ml/min; numbers of revolution, 3,000 rpm. The disrupted cells were removed by centrifugation (10,000 rpm, 20 min.). The supernatant obtained (1280 ml) had 75 units of acylamino acid racemase activity and 1,500 units of L-aminoacylase activity. To the cell-free extract (1280 ml), 500 g of $(NH_4)_2SO_4$ was added to give 60% saturation by the same manner described in Example 2. The resultant precipitate was collected by centrifugation (10,000 rpm, 30 min) and dissolved in 600 ml of 50 mM phosphate buffer (pH 7.0). The enzyme solution was dialyzed with cellulose bags against the same buffer for 18 hours. The desalted enzyme solution was charged to a column (3cm×30 cm) of DEAE-Toyopearl 650M (Tosoh Co., Japan) equilibrated with 50 mM phosphate buffer (pH 7.0). The column was washed with 1,000 ml of the same buffer and furthermore washed with 1,000 ml of 20 mM Tris-HCl buffer (pH 7.5) containing 1 mM $CoCl_2$.

The total activites of acylamino acid racemase and L-aminoacylase adsorbed on this column were 43 and 800 units, respectively. While the above column is keeping at 28° C., 2,000 ml of 20 mM Tris-HCl buffer (pH 7.5) containing 0.5% N-chloroacetyl-D-valine, 1 mM $CoCl_2$, and 1 μg/ml dihydrostreptomycin sulfate was passed through the column at the flow rate of 60 ml/hour. After the end of reaction, the column was washed with 500 ml of 20 mM Tris-HCl buffer (pH 7.5) containing 1mM $CoCl_2$. The eluate was collected and analyzed with high performance liquid chromatography. No N-chloroacetyl-D-valine was detected at all in this solution. After the eluate was concentrated in vacuo, cold ethanol was added to it. White precipitated solids obtained were collected by filtration, washed with cold ethanol and dissolved in a small amount of water-ethanol. Standing on it at 4° C., the colorless leaflet crystals were obtained. The crystals were collected by filtration and dried. Amount of yield is 4.5 g. The melting point was 315° C. (decomposition).

$[\alpha]_D^{25} +6.4°$ (c=1, $H_2O$) The sample solution of this crystals showed the same retention time and Rf-value of the standard sample of L-valine in high performance liquid chromatography and thin layer chromatography, respectively.

What is claimed is:

1. An enzyme acylamino acid racemase which has the following properties:
   (1) converting D-N-acyl-α-aminocarboxylic acid of the formula:

wherein X is carboxylic acid derived acyl which may be substituted, and R is (a) straight or branched-chain $C_{1-6}$ alkyl, (b) $C_{1-3}$ alkyl which is substituted with hydroxyl, $C_{1-3}$ alkylthio, thiol, phenyl, hydroxyphenyl or indolyl, or (c) $C_{1-4}$ alkyl which is substituted with amino, carboxyl, guanidyl or imidazolyl; to the corresponding L-N-acyl-α-aminocarboxylic acid of the formula:

wherein X and R have the same meaning as defined above;
   (2) converting L-N-acyl-α-aminocarboxylic acid of the formula:

wherein X and R have the same meaning as defined above;
   to the corresponding D-N-acyl-α-aminocarboxylic acid of the formula:

wherein X and R have the same meaning as defined above.
   (3) not converting D-α-amino acid to the corresponding L-α-amino acid, and
   (4) not converting L-α-amino acid to the corresponding D-α-amino acid.

2. The acylamino acid racemase according to claim 1, wherein X is $C_{1-3}$ alkanoyl or benzoyl which may be substituted with halogen, $C_{1-3}$ alkyl, $C_{1-3}$ alkoxyl or/and nitro.

3. The acylamino acid racemase according to claim 1, which is a fermentation product produced by a microorganism capable of producing the same.

4. The acylamino acid racemase according to claim 1, which further contains aminoacylase.

5. A method for producing the acylamino acid racemase according to claim 1, which comprises cultivating a microorganism capable of producing said enzyme in a culture medium to accumulate said enzyme in the broth and harvesting said enzyme.

6. A method for producing optically acative D- or L-amino acid which comprises contacting the acylamino acid racemase according to claim 1 with DL-N-acyl-α-aminocarboxylic acid in the presence of D-or L-aminoacylase.

* * * * *